(12) United States Patent
Farmer

(10) Patent No.: US 6,584,969 B2
(45) Date of Patent: Jul. 1, 2003

(54) INHALATION THERAPY ASSEMBLY AND METHOD

(76) Inventor: Michael W. Farmer, 1325 Meadowbrook Dr., King, NC (US) 27021

( * ) Notice: Subject to any disclaimer, the term of this patent is extended or adjusted under 35 U.S.C. 154(b) by 0 days.

(21) Appl. No.: 09/917,323

(22) Filed: Jul. 30, 2001

(65) Prior Publication Data

US 2002/0069870 A1 Jun. 13, 2002

Related U.S. Application Data

(63) Continuation-in-part of application No. 09/730,997, filed on Dec. 7, 2000, now Pat. No. 6,494,202.

(51) Int. Cl.$^7$ ............................................. A61M 11/00
(52) U.S. Cl. ........................... 128/200.22; 128/200.28; 128/200.13
(58) Field of Search ............................. 128/194, 200.22, 128/203.12, 200.13

(56) References Cited

U.S. PATENT DOCUMENTS

| | | | |
|---|---|---|---|
| 3,874,379 A | * | 4/1975 | Enfield et al. ............... 128/194 |
| 5,020,530 A | | 6/1991 | Miller |
| 5,479,920 A | | 1/1996 | Piper et al. |
| 5,842,467 A | | 12/1998 | Greco |
| 5,853,002 A | | 12/1998 | Kawasaki |
| 5,894,841 A | * | 4/1999 | Voges ..................... 128/203.12 |
| 5,988,160 A | * | 11/1999 | Foley et al. ............ 128/200.22 |

OTHER PUBLICATIONS

Photocopy of Aerovent Aerosol Holding Chamber Box (Undated).
Aerochamber Valved Holding Chamber ("VHC") Instructions Issue Date Sep. 1999.
Aerochamber MV Aserosol Holding Chamber ("AHC") Instructions Issue Date Jun.1999.
Aerochamber with Small Mask Instructions Issued Date Jan. 4, 1996.

* cited by examiner

*Primary Examiner*—Henry Bennett
*Assistant Examiner*—Sabrina Dagostino

(57) ABSTRACT

The inhalation therapy assembly and method of use described herein increases the efficiency of metered dose inhalers by allowing delivery of the doses to a collapsible reservoir which can be manually pumped, ensuring that medicants contained therein are properly and completely delivered to the patient. Terminal and proximal valves of the one-way diaphragm type allow flow of the aerosol medicants while preventing improper expulsion. An exhalation valve is adjustable to ensure the patient exhales suitably to permit proper medicant absorption. A conventional metered dosage inhaler having an approved FDA canister provides proper dosage to the patient and is joined to the collapsible reservoir by a connector having a plurality of apertures for receiving the MDI and an accessory T-fitting.

9 Claims, 5 Drawing Sheets

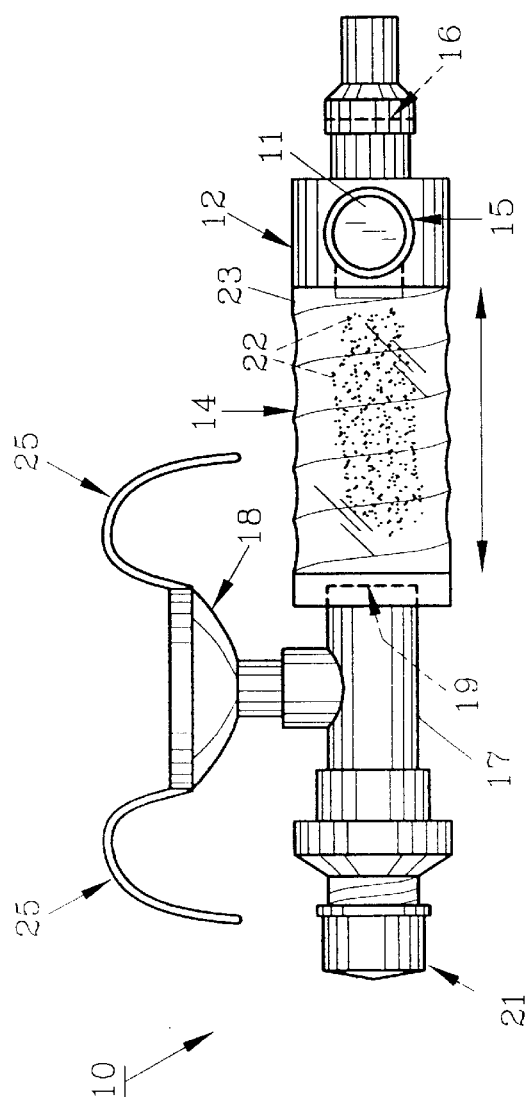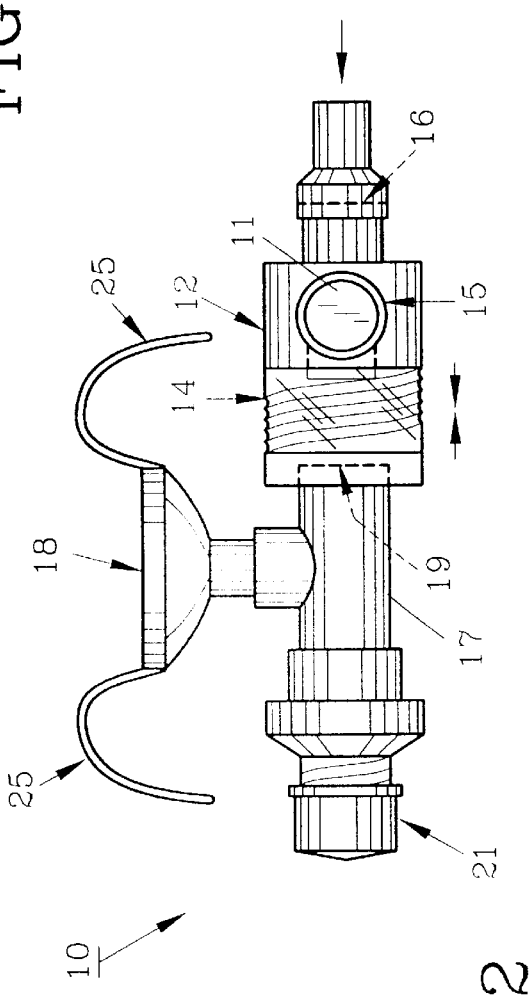

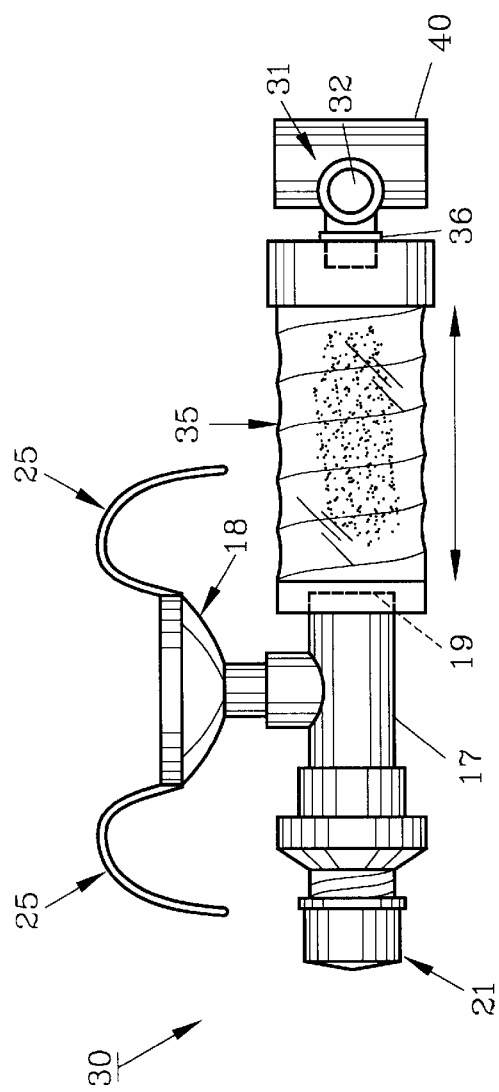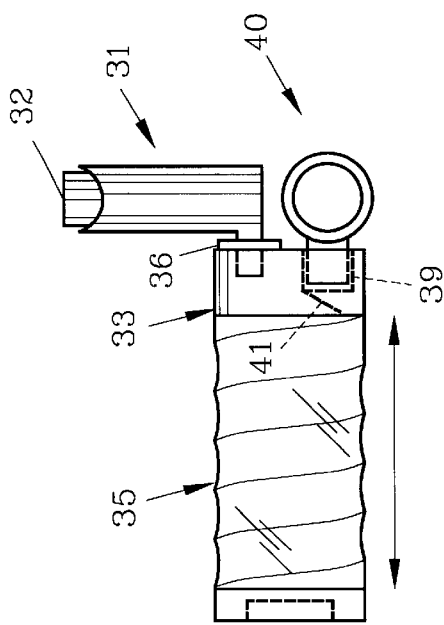

INHALATION THERAPY ASSEMBLY AND METHOD

This is a continuation-in-part of patent application Ser. No. 09/730,997 filed Dec. 7, 2000 now U.S. Pat. No. 6,494,202.

FIELD OF THE INVENTION

The invention herein pertains to inhalation therapy and particularly pertains to an assembly and method which utilizes a manual pumping action to ensure complete medication dosage delivery to the patient.

DESCRIPTION OF THE PRIOR ART AND OBJECTIVES OF THE INVENTION

Medications for bronchitis and other common respiratory ailments are conventionally sold in metered dose inhalers (MDI) which have pressurized canisters to release a prescribed dosage quantity of medicants upon each manual activation. Many patients frequently use MDIs for easy, portable, self-medication. Other patients with more serious health conditions utilize various types of inhalation therapy devices such as set forth in U.S. Pat. Nos. 5,020,530 and 5,479,920. In addition, U.S. Pat. No. 5,842,467 provides a MDI in combination with a manual breathing unit. Other common types of mechanical respiratory devices include electrical powered ventilators, oxygen tanks and the like.

It is commonplace to utilize a collapsible reservoir with an MDI canister for discharge therein. Such devices are often used in ventilator breathing circuits. It is also usual to provide a rigid, transparent, cylindrical reservoir with a MDI canister for containment of the medicants before such enters the patient's lungs.

Conventional methods of delivering respiratory medicants often work very well under normal circumstances with a cooperative patient. However, young children are often frightened by inhalation apparatus which are attached to their face and as a result hold their breath, preventing intake of the medicants. Sometimes elderly patients become obstinate and will not cooperate with medical personnel or some, for physical reasons have difficulty in breathing properly. Breathing too fast can also cause problems in that the medicants are taken into the lungs and are exhaled too quickly, before being absorbed. Under these conditions the medicants are not absorbed and the patient does not ultimately benefit from the prescribed dosage. Other patients also lack adequate muscle tone for deep breaths due to advanced disease status or heavy sedation.

Thus, with the problems and difficulties of prior art inhalation therapy devices, the present invention was conceived and one of its objectives is to provide an inhalation therapy assembly and method which will conveniently and easily allow the patient to receive the proper prescribed medicant dosage.

It is also an objective of the present invention to provide an inhalation assembly which can be used with either a facial mask or an endotrachael tube.

It is yet a further objection of the present invention to provide an inhalation therapy assembly which includes a collapsible reservoir which can be used to manually pump medicants to the patient.

It is still another objective of the present invention to provide an inhalation therapy assembly which utilizes a standard peep valve which is adjustable to provide the needed resistance for a particular patient.

It is a further objective of the present invention to provide an alternative inhalation therapy assembly and method utilizing a conventional MDI which can be connected to an inhalation therapy assembly having a collapsible reservoir to ensure FDA approved dosage amounts.

Various other objectives and advantages of the present invention will become apparent to those skilled in the art as a more detailed description is set forth below.

SUMMARY OF THE INVENTION

The aforesaid and other objectives are realized by providing an inhalation assembly which includes a MDI canister housing which is affixed to a conventional coil spring supported, transparent, flexible reservoir for receiving medicants therefrom. In an alternate embodiment a commercially available MDI and cannister is utilized. As the medicants are released from the pressurized aerosol canister, such medicants flow into the expanded reservoir and a terminal diaphragm valve in communication therewith closes due to the pressure associated therewith. As the patient breathes in, a proximal one-way valve on the reservoir opens to allow the medicants to flow from the reservoir to the lungs of the patient through a means connected to a delivery tube, either an endotracheal tube or a conventional facial mask. An adjustable exhalation valve prevents the patient from over breathing, i.e., expiring the medicants too quickly. Should there be a problem with the patient's breathing, through either lack of cooperation, fear or voluntary physical restraints, the assisting medical personnel can simply "pump" the assembly manually by urging the reservoir to a collapsed position, thereby driving the medicants from the reservoir through the proximal one-way valve into the delivery tube which is attached to for example, a facial mask. The reservoir, which is spring loaded will then recover and the pumping action is repeated until all the medicants are introduced into the patient's lungs, thereby ensuring the patient of receiving the full dosage prescribed, without significant residual amounts remaining in the reservoir.

In an alternate embodiment, a typical metered dose inhaler and pressurized canister is employed to insure FDA approved doses are delivered. An MDI canister is thereby releasably joined to the terminal end of a cylindrical reservoir by a connector which includes an aperture for the outlet of the MDI and for an accessory T-fitting for supplying supplemental oxygen, if needed.

BRIEF DESCRIPTION OF THE DRAWINGS

FIG. 1 shows a top view of the preferred form of the invention with the reservoir in an extended state;

FIG. 2 illustrates the invention as shown in FIG. 1 but with the reservoir in a collapsed posture;

FIG. 5 shows an alternate inhalation therapy assembly for use with a conventional MDI;

FIG. 8 demonstrates the inhalation therapy assembly as seen in FIG. 6 but with the MDI and accessory T-fitting attached.

DETAILED DESCRIPTION OF THE PREFERRED EMBODIMENT AND OPERATION OF THE INVENTION

Figure 3:
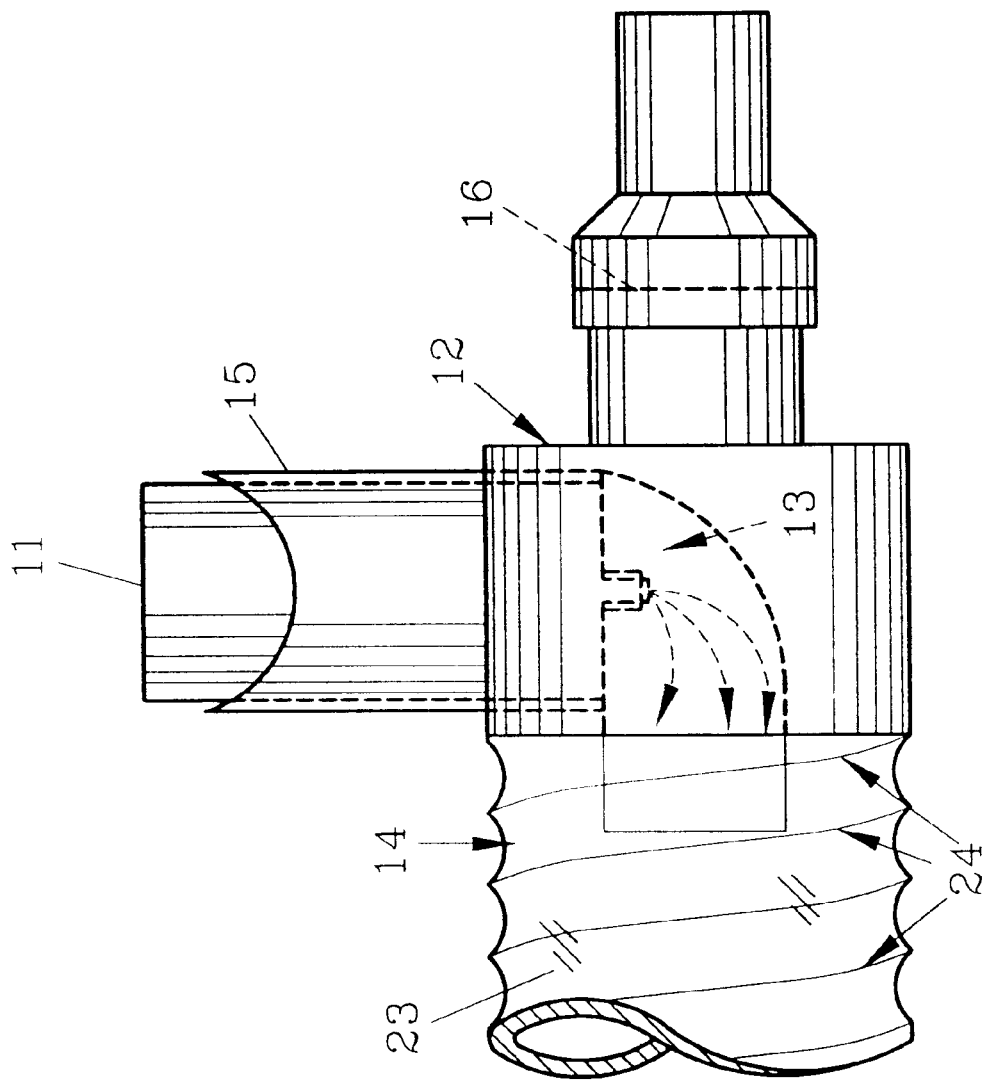
FIG. 3 depicts an enlarged partial side view of the reservoir and MDI canister housing.
Figure 4:
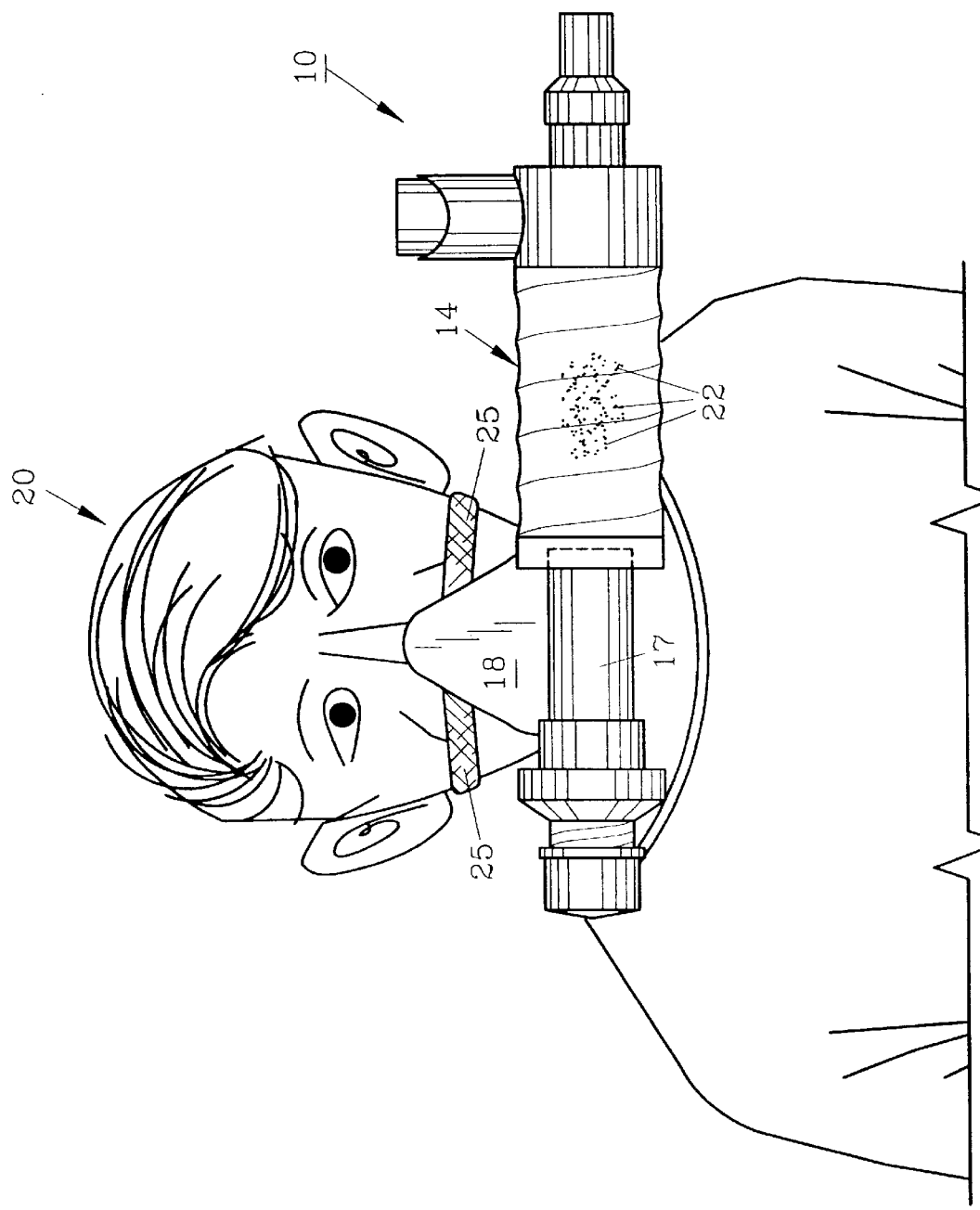
FIG. 4 pictures the apparatus as shown in FIG. 1 in place on a male patient.

For a better understanding of the invention and its operation, turning now to the drawings, FIG. 1 illustrates preferred inhalation therapy assembly 10 having an aerosol metered dose inhaler (MDI) canister 11 positioned in receptacle 15 of MDI housing 12 for delivering medicants 22 through housing channel 13 (FIG. 3) into collapsible reservoir 14. Standard terminal one-way diaphragm valve 16 is in fluid communication with collapsible reservoir 14 to prevent fluids contained within reservoir 14 from escaping and to allow entry of air into reservoir 14 as it is expanded. At the other end of reservoir 14, proximal one-way diaphragm valve 19 is connected to T-shaped delivery tube 17 as seen in FIGS. 1 and 2. T-shaped delivery tube 17 provides a passageway for directing medicants 22 to patient 20 (FIG. 4) through a means to connect to a patient, preferably mask 18. As aerosol medicants 22 are often not directly or efficiently delivered to patient 20, collapsible reservoir 14 can be manually collapsed and extended (pumped) in order to ensure substantial delivery of medicants 22 to patient 20. This is of particular importance for very young patients that might hold their breath or older patients that are uncooperative or lack sufficient muscle tone for a full spontaneous inhalation. Collapsible reservoir 14 is conventional and includes an outer, thin, transparent, polymeric wall 23 which is internally supported by metal coil spring 24 as seen in FIG. 3.

After patient 20 inhales medicants 22 from reservoir 14, exhaled gases are then forced through T-shaped delivery tube 17 and encounter exhalation or peep valve 21 as shown in FIG. 2 which provides resistance to the exhaled gases, as proximal valve 19 is closed. This created resistance increases the time medicants 22 remain in the lungs of patient 20 and assists in the absorption thereof.

The preferred method of use of inhalation assembly 10 comprises attaching mask 18 to patient 20 via straps 25 or the like which may have a means to connect thereon such as hook and loop fasteners, a buckle, snaps or the like (not seen). Next, MDI canister 11 is positioned in receptacle 15 of housing 12 with reservoir 14 fully expanded as shown in FIG. 1. By depressing aerosol MDI canister 11 within receptacle 15 the MDI canister valve (not shown) opens, and medicants 22 contained therein which may be for the treatment of bronchitis or other ailments passes through channel 13 into collapsible reservoir 14. Normal breathing by patient 20 draws medicants 22 from reservoir 14 through mask 18 and on into the lungs of patient 20 as intended. After inhaling, patient 20 then exhales and one-way proximal diaphragm valve 19 as shown in FIGS. 1 and 2 prevents exhaled gases from entering reservoir 14. Rather, such gases are passed through standard exhalation valve 21 which has been adjusted for suitable resistance, depending on the specific requirements of patient 20. For example, if the patient is breathing normally, then valve 21 would be positioned at a relative low rating (such as at 5 cm of water pressure). This setting would also be used when assembly 10 is used with an endotracheal tube. For a greater resistance, that is, to prevent the patient from exhaling too quickly and the medicant 22 being only partially absorbed due to the short time period in the lungs, exhalation valve 21 is adjusted for a greater resistance, up to for example, 20 cm of water pressure. This high resistance slows the exhalation of the patient, thereby allowing the medicants to be more fully absorbed.

In the event a patient is uncooperative, or has trouble breathing once medicants 22 have been released into reservoir 14, a nurse or other medical personnel can manually "pump" reservoir 14 by grasping canister housing 12 and urging reservoir 14 into a collapsed posture as shown in FIG. 2. Terminal valve 16 which has been closed by the pressure created in reservoir 14 by the release of medicants 22 from pressurized aerosol MDI canister 11, remains closed as reservoir 14 is collapsed. Once collapsed, reservoir 14 can be rapidly expanded by manually urging it outwardly, which allows terminal valve 16 to open and permits air to flow therethrough into reservoir 14. As would be understood, proximal one-way valve 19 likewise opens as air is forced therethrough by collapsing reservoir 14 and allows medicants 22 to pass into T-shaped delivery tube 17 and on to patient 20. Additional collapsing and expansion of reservoir 14 can be carried out as required and, if additional doses of medicants 22 are needed, MDI canister 11 is manually pressed downwardly to release medicants 22 therefrom into reservoir 14 as hereinbefore explained.

Thus, inhalation assembly 10 provides an easy method for ensuring both medicant delivery and absorption by patient 20. Also, the device is conveniently used with patients requiring an endotracheal tube (not seen) which is attached to T-shaped delivery tube 17 in place of mask 18.

Figure 7:
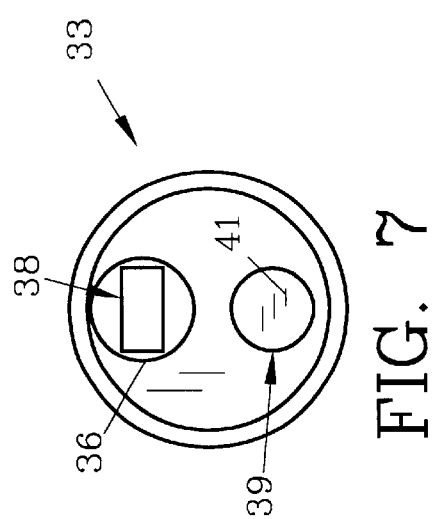
FIG. 7 illustrates an end view of the MDI connector as seen in FIG. 6 along lines 7—7.
Figure 6:
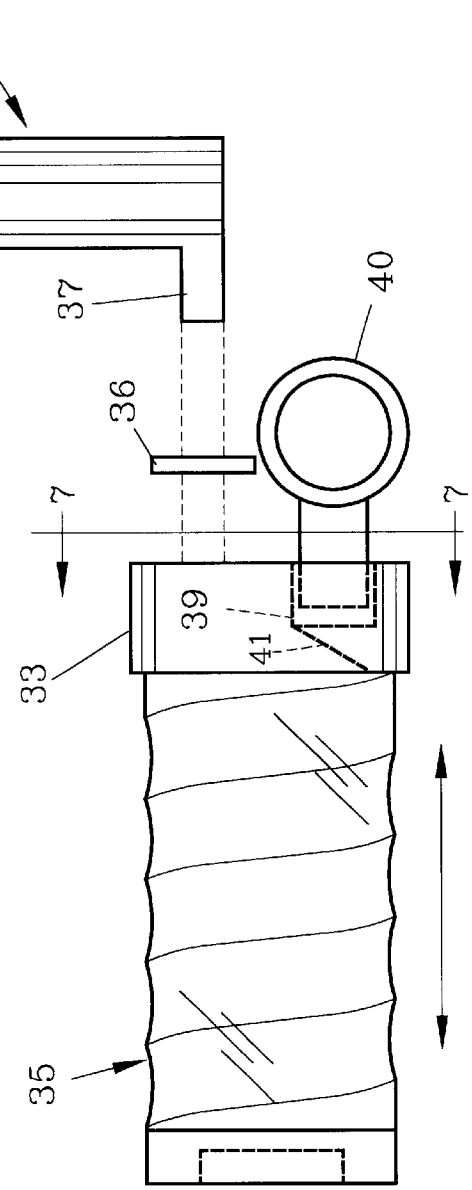
FIG. 6 depicts a view of the fragmented assembly as seen in FIG. 5 in enlarged fashion.

In an alternate embodiment of the invention as shown in FIGS. 5–8, alternate inhalation therapy assembly 30 is shown in FIG. 5 having a separately furnished standard aerosol metered dose inhaler (MDI) 31 with canister 32 therein. Metered dose inhaler 31 is produced by a number of pharmaceutical companies and is manually operated by depressing canister 32 to deliver a specific, FDA approved dosage of medicants through nozzle 37 (FIG. 6). Connector 33 formed from plastic with a somewhat resilient or flexible, circular adapter 36 surrounding opening 38 is affixed to collapsible reservoir 35 which performs in the same manner as previously described regarding collapsible reservoir 14 of the preferred embodiment. Connector 33 as shown in FIG. 7 includes aperture 38 for receiving nozzle 37 of MDI 31 as shown in FIG. 6 and also includes inlet 39 with one-way valve 41 (FIG. 8) which can be used for receiving accessory T-fitting 40 (shown in FIGS. 6 and 8). T-fitting 40 may be used for an auxiliary oxygen supply hook-up. Flap valve 41 closes as reservoir 35 is collapsed. Thus, flap valve 41 is normally closed and helps prevent the escape of medicants from reservoir 35. When using alternate inhalation therapy assembly 30, the user receives the prescribed dosage of medicants from canister 32 as approved with MDI 31. A consumer can purchase a standard MDI and canister and use it with inhalation therapy assembly 30 for improved accuracy in dosage and for convenience purposes. Connector 33 may have other possibly uses, such as with a military gas mask for emergency medicine delivery in conjunction with an approved MDI and canister.

The illustrations and examples provided herein are for explanatory purposes and are not intended to limit the scope of the appended claims.

I claim:
1. An inhalation assembly comprising:
    a collapsible reservoir, said reservoir comprising a flexible wall, an MDI connector, said MDI connector joined to said collapsible reservoir, a delivery tube, said delivery tube joined to said reservoir whereby medicants can pass through said MDI connector into said reservoir for continued passage through said delivery tube to the patient.
2. The inhalation assembly of claim 1 wherein said MDI connector defines an MDI aperture.

3. The inhalation assembly of claim 1 wherein said MDI connector defines an accessory connector aperture.

4. The inhalation assembly of claim 1 wherein said flexible wall is spring supported.

5. The inhalation assembly of claim 4 wherein said flexible wall is transparent.

6. An inhalation assembly for delivering medicants from an MDI to a patient comprising;

an MDI connector, a collapsible reservoir, said reservoir comprising a flexible wall, said. MDI connector attached to said collapsible reservoir, a terminal one-way valve, said terminal one-way valve In communication with said collapsible reservoir, a delivery tube, a proximal one-way valve, said delivery tube connected to said collapsible reservoir through said proximal one-way valve, means to connect a patient, said connecting means attached to said delivery tube, and an exhalation valve, said exhalation valve connected to said delivery tube.

7. The inhalation assembly of claim 6 wherein delivery tube is T-shaped and said exhalation valve in axial alignment along said delivery tube with said collapsible reservoir.

8. The inhalation assembly of claim 7 wherein said flexible wall is spring supported.

9. The inhalation assembly of claim 8 wherein said flexible wall is transparent.

\* \* \* \* \*